(12) United States Patent
Quintero et al.

(10) Patent No.: US 10,993,708 B2
(45) Date of Patent: May 4, 2021

(54) SKIN CLOSURE DEVICES WITH INTERRUPTED CLOSURE

(71) Applicant: Ethicon, Inc., Somerville, NJ (US)

(72) Inventors: Julian Quintero, Flemington, NJ (US); Leo B. Kriksunov, Ithaca, NY (US); Elena Wolfe, Boston, MA (US)

(73) Assignee: Ethicon, Inc., Somerville, NJ (US)

( * ) Notice: Subject to any disclaimer, the term of this patent is extended or adjusted under 35 U.S.C. 154(b) by 219 days.

(21) Appl. No.: 16/050,205

(22) Filed: Jul. 31, 2018

(65) Prior Publication Data
US 2020/0038006 A1    Feb. 6, 2020

(51) Int. Cl.
*A61B 17/00* (2006.01)
*A61F 13/02* (2006.01)
*A61F 13/00* (2006.01)

(52) U.S. Cl.
CPC .... *A61B 17/00491* (2013.01); *A61F 13/0206* (2013.01); *A61F 13/0253* (2013.01); *A61B 2017/00495* (2013.01); *A61F 2013/00182* (2013.01)

(58) Field of Classification Search
CPC ............... A61B 17/00; A61B 17/0057; A61B 17/00491; A61B 2017/00495; A61B 2017/00637; A61B 2017/0065; A61L 24/00; A61F 13/0206; A61F 13/0253; A61F 2013/00182
See application file for complete search history.

(56) References Cited

U.S. PATENT DOCUMENTS

| | | | |
|---|---|---|---|
| 167,162 | A | 8/1875 | French |
| 2,508,855 | A | 5/1950 | Brown |
| 2,721,858 | A | 10/1955 | Joyner et al. |
| 2,722,220 | A | 11/1955 | Mestrand |
| 2,807,262 | A | 9/1957 | Lew |
| 2,905,174 | A | 5/1959 | Smith |
| 3,254,111 | A | 5/1966 | Hawkins et al. |
| 3,402,716 | A | 9/1968 | Baxter |
| 3,520,300 | A | 7/1970 | Flower, Jr. |

(Continued)

FOREIGN PATENT DOCUMENTS

| | | |
|---|---|---|
| CA | 2262408 | 8/2000 |
| CN | 102755216 A | 10/2012 |

(Continued)

OTHER PUBLICATIONS

JP 7040744, 1995, English claims.
(Continued)

*Primary Examiner* — Vi X Nguyen

(57) ABSTRACT

A device for application onto incisions or wounds with a liquid rapidly polymerizable adhesive for forming skin closure systems, having a flat porous mesh elongated along a longitudinal axis and having an upper side and an opposing lower or wound facing side and a central portion in immediate vicinity of the axis; further having a plurality of pores and windows in said mesh, said windows substantially larger than said pores and arranged along said longitudinal axis in said central portion; a crosslinking or polymerization accelerator or initiator disposed in or on the mesh; and a pressure sensitive adhesive disposed on at least a portion of the lower surface of the mesh.

15 Claims, 7 Drawing Sheets

(56) References Cited

U.S. PATENT DOCUMENTS

| | | | |
|---|---|---|---|
| 3,731,683 A | 5/1973 | Zaffaroni | |
| 3,888,247 A | 6/1975 | Stenvall | |
| 3,940,362 A | 2/1976 | Overhults | |
| 3,983,878 A | 10/1976 | Kawchitch | |
| 3,995,641 A | 12/1976 | Kronenthal et al. | |
| 4,068,664 A | 1/1978 | Sharp et al. | |
| 4,080,348 A | 3/1978 | Korpman | |
| 4,126,130 A | 11/1978 | Cowden et al. | |
| 4,140,115 A | 2/1979 | Schonfeld | |
| 4,263,906 A | 4/1981 | Finley | |
| 4,313,865 A | 2/1982 | Teramoto et al. | |
| 4,340,043 A | 7/1982 | Seymour | |
| 4,364,876 A | 12/1982 | Kimura et al. | |
| 4,390,519 A | 6/1983 | Sawyer | |
| 4,460,369 A | 7/1984 | Seymour | |
| 4,560,723 A | 12/1985 | Millet et al. | |
| 4,584,355 A | 4/1986 | Blizzard et al. | |
| 4,585,836 A | 4/1986 | Homan et al. | |
| 4,591,622 A | 5/1986 | Blizzard et al. | |
| 4,612,230 A | 9/1986 | Liland et al. | |
| 4,614,183 A | 9/1986 | McCracken et al. | |
| 4,630,603 A | 12/1986 | Greenway | |
| 4,655,767 A | 4/1987 | Woodard et al. | |
| 4,671,266 A | 6/1987 | Legnyel et al. | |
| 4,720,513 A | 1/1988 | Kameyama et al. | |
| 4,733,659 A | 3/1988 | Edenbaum et al. | |
| 4,767,401 A | 8/1988 | Seiderman | |
| 4,793,887 A | 12/1988 | Card et al. | |
| 4,793,888 A | 12/1988 | Card et al. | |
| 4,795,435 A * | 1/1989 | Steer | A61M 1/0088 600/573 |
| 4,852,571 A | 8/1989 | Gadsby et al. | |
| 4,867,747 A | 9/1989 | Yarger | |
| 4,872,450 A | 10/1989 | Austad | |
| 4,950,282 A | 8/1990 | Beisang et al. | |
| 4,966,605 A | 10/1990 | Thieler | |
| 4,999,235 A | 3/1991 | Lunn et al. | |
| 5,035,687 A | 7/1991 | Sandbank | |
| 5,059,424 A | 10/1991 | Cartmell et al. | |
| 5,086,763 A | 2/1992 | Hathman | |
| 5,088,483 A | 2/1992 | Heinecke | |
| 5,106,362 A | 4/1992 | Gilman | |
| 5,125,907 A | 6/1992 | Philpott | |
| 5,164,444 A | 11/1992 | Bernard | |
| 5,173,302 A | 12/1992 | Holmblad et al. | |
| 5,232,958 A | 8/1993 | Mallya et al. | |
| 5,254,132 A | 10/1993 | Barley et al. | |
| 5,259,835 A | 11/1993 | Clark et al. | |
| 5,266,371 A | 11/1993 | Sugii et al. | |
| 5,308,313 A | 5/1994 | Karami et al. | |
| 5,328,687 A | 7/1994 | Leung et al. | |
| 5,336,209 A | 8/1994 | Porzilli | |
| 5,415,626 A | 5/1995 | Goodman et al. | |
| 5,429,592 A | 7/1995 | Jensen | |
| 5,445,597 A | 8/1995 | Clark et al. | |
| 5,449,340 A | 9/1995 | Tollini | |
| D363,126 S * | 10/1995 | Dusek | |
| 5,456,660 A | 10/1995 | Reich et al. | |
| 5,476,440 A | 12/1995 | Edenbaum | |
| 5,486,547 A | 1/1996 | Matsuda et al. | |
| 5,571,079 A | 11/1996 | Bello et al. | |
| 5,575,997 A | 11/1996 | Leung et al. | |
| 5,582,834 A | 12/1996 | Leung et al. | |
| 5,599,858 A | 2/1997 | Buchanan et al. | |
| 5,620,702 A | 4/1997 | Podell et al. | |
| 5,623,011 A | 4/1997 | Bernard | |
| 5,624,669 A | 4/1997 | Leung et al. | |
| D382,343 S * | 8/1997 | Wandell et al. | |
| 5,653,769 A | 8/1997 | Barley, Jr. et al. | |
| D383,211 S * | 9/1997 | Dunshee et al. | |
| 5,662,599 A | 9/1997 | Reich et al. | |
| D387,169 S * | 12/1997 | Dunshee et al. | |
| D389,244 S * | 1/1998 | Dunshee et al. | |
| 5,705,551 A | 1/1998 | Sasaki et al. | |
| D391,639 S * | 3/1998 | Dunshee et al. | |
| 5,749,895 A | 5/1998 | Sawyer et al. | |
| 5,762,955 A | 6/1998 | Smith | |
| 5,780,048 A | 7/1998 | Lee | |
| 5,782,788 A | 7/1998 | Widemire | |
| 5,823,983 A | 10/1998 | Rosofsky et al. | |
| 5,823,986 A | 10/1998 | Peterson | |
| D402,371 S * | 12/1998 | Haynes et al. | |
| 5,861,348 A | 1/1999 | Kase | |
| 5,876,745 A | 3/1999 | Muraoka et al. | |
| 5,902,443 A | 5/1999 | Kanakubo et al. | |
| 5,928,611 A | 7/1999 | Leung | |
| 5,931,800 A | 8/1999 | Rasmussen et al. | |
| 5,947,917 A | 9/1999 | Carté et al. | |
| 5,951,505 A | 9/1999 | Gilman et al. | |
| 5,998,694 A | 12/1999 | Jensen et al. | |
| D424,699 S * | 5/2000 | Allen | |
| 6,093,465 A | 7/2000 | Gilchrist et al. | |
| 6,125,265 A | 9/2000 | Yamamoto et al. | |
| 6,140,548 A | 10/2000 | Hansen et al. | |
| 6,143,352 A | 11/2000 | Clark et al. | |
| 6,155,265 A | 12/2000 | Hammerslag | |
| 6,183,593 B1 | 2/2001 | Narang et al. | |
| 6,217,603 B1 | 4/2001 | Clark et al. | |
| 6,238,692 B1 | 5/2001 | Smith | |
| 6,245,960 B1 | 6/2001 | Eaton | |
| 6,284,941 B1 | 9/2001 | Cox et al. | |
| 6,310,166 B1 | 10/2001 | Hickey et al. | |
| 6,329,564 B1 | 12/2001 | Lebner | |
| 6,352,704 B1 | 3/2002 | Nicholson et al. | |
| 6,410,818 B1 | 6/2002 | Oyaski | |
| 6,439,789 B1 | 8/2002 | Balance et al. | |
| D463,564 S * | 9/2002 | Siegwart et al. | |
| 6,455,064 B1 | 9/2002 | Narang et al. | |
| 6,479,725 B1 | 11/2002 | Brothers | |
| 6,482,431 B2 | 11/2002 | Smith | |
| 6,512,023 B1 | 1/2003 | Malofsky et al. | |
| D472,319 S | 3/2003 | Oltmann | |
| 6,559,350 B1 | 5/2003 | Tetreault et al. | |
| 6,579,469 B1 | 6/2003 | Nicholson et al. | |
| 6,582,713 B2 | 6/2003 | Newell et al. | |
| 6,589,269 B2 | 7/2003 | Zhu et al. | |
| 6,595,940 B1 | 7/2003 | D'Alessio et al. | |
| 6,596,917 B2 | 7/2003 | Oyaski | |
| 6,599,318 B1 | 7/2003 | Gabbay | |
| 6,620,846 B1 | 9/2003 | Jonn et al. | |
| 6,632,450 B1 | 10/2003 | Gregory | |
| 6,635,272 B2 | 10/2003 | Leaderman | |
| 6,652,559 B1 | 11/2003 | Tetreault et al. | |
| 6,667,051 B1 | 12/2003 | Gregory | |
| 6,712,839 B1 | 3/2004 | Lönne | |
| 6,787,682 B2 | 9/2004 | Gilman | |
| 6,837,027 B2 | 1/2005 | Hickey | |
| 6,942,683 B2 | 9/2005 | Dunshee | |
| D520,639 S * | 5/2006 | Dodd et al. | |
| 7,044,982 B2 | 5/2006 | Milbocker | |
| 7,066,934 B2 | 6/2006 | Kirsch | |
| 7,122,712 B2 | 10/2006 | Lutri et al. | |
| 7,144,390 B1 | 12/2006 | Hannigan et al. | |
| 7,164,054 B2 | 1/2007 | Mori et al. | |
| D548,348 S * | 8/2007 | Nash | |
| 7,252,837 B2 | 8/2007 | Guo et al. | |
| D562,461 S * | 2/2008 | Nash et al. | |
| 7,371,400 B2 | 5/2008 | Borenstein et al. | |
| D574,962 S * | 8/2008 | Atkins et al. | |
| D580,553 S * | 11/2008 | Nash | |
| 7,457,667 B2 | 11/2008 | Skiba | |
| D582,561 S * | 12/2008 | Sachi | |
| D584,415 S * | 1/2009 | Sachi | |
| 7,576,257 B2 | 8/2009 | LaGreca, Sr. | |
| D611,156 S * | 3/2010 | Dunshee | |
| 7,713,463 B1 | 5/2010 | Reah et al. | |
| D618,810 S * | 6/2010 | Tanigawa et al. | |
| 7,943,811 B2 | 5/2011 | Da Silva Macedo, Jr. | |
| 7,981,136 B2 | 7/2011 | Weiser | |
| 7,982,087 B2 | 7/2011 | Greener et al. | |
| D646,789 S * | 10/2011 | Barth | |
| 8,343,606 B2 | 1/2013 | Marchitto et al. | |
| 8,353,966 B2 | 1/2013 | Day et al. | |
| D679,098 S * | 4/2013 | Ogawa | |

(56) References Cited

U.S. PATENT DOCUMENTS

| | | | |
|---|---|---|---|
| D679,402 S * | 4/2013 | Conrad-Vlasak et al. | |
| D679,403 S * | 4/2013 | Heinecke et al. | |
| D679,819 S | 4/2013 | Peron | |
| D679,820 S | 4/2013 | Peron | |
| 8,528,730 B2 | 9/2013 | Grossman | |
| D691,730 S | 10/2013 | Smith et al. | |
| D692,566 S | 10/2013 | Adoni | |
| D693,010 S | 11/2013 | Mosa et al. | |
| D694,892 S | 12/2013 | Chan et al. | |
| 8,603,053 B2 | 12/2013 | Riesinger | |
| D697,216 S | 1/2014 | Chan et al. | |
| 8,642,831 B2 | 2/2014 | Larsen et al. | |
| 8,663,171 B2 | 3/2014 | Tambourgi et al. | |
| D707,829 S | 6/2014 | Chan et al. | |
| D708,751 S | 7/2014 | Chan et al. | |
| 8,777,986 B2 | 7/2014 | Straehnz et al. | |
| D712,045 S | 8/2014 | Thornton | |
| D713,967 S | 9/2014 | Adoni | |
| 8,884,094 B2 | 11/2014 | Lockwood et al. | |
| 9,000,251 B2 | 4/2015 | Murphy et al. | |
| RE45,510 E | 5/2015 | Hisamitsu | |
| D728,803 S | 5/2015 | Sinda et al. | |
| D745,688 S | 12/2015 | Chan et al. | |
| D745,689 S | 12/2015 | Chan et al. | |
| D746,479 S | 12/2015 | Arefieg | |
| D750,789 S | 3/2016 | Mackay et al. | |
| D757,950 S | 5/2016 | Karlsson et al. | |
| 9,339,417 B2 | 5/2016 | Ogawa | |
| 9,381,284 B2 | 7/2016 | Cornet et al. | |
| 9,492,171 B2 | 11/2016 | Patenaude | |
| 9,623,142 B2 | 4/2017 | Jonn et al. | |
| 9,655,622 B2 | 5/2017 | Jonn et al. | |
| 2001/0002432 A1 | 5/2001 | Bugge | |
| 2001/0028943 A1 | 10/2001 | Mashiko et al. | |
| 2001/0037077 A1 | 11/2001 | Wiemken | |
| 2002/0019652 A1 | 2/2002 | DaSilva et al. | |
| 2002/0037310 A1 | 3/2002 | Jonn et al. | |
| 2002/0185396 A1 | 12/2002 | Mainwaring et al. | |
| 2002/0192107 A1 | 12/2002 | Hickey | |
| 2002/0193721 A1 | 12/2002 | VanDruff | |
| 2003/0031499 A1 | 2/2003 | Heard et al. | |
| 2003/0093024 A1 | 5/2003 | Falleiros et al. | |
| 2003/0100955 A1 | 5/2003 | Greenawalt et al. | |
| 2003/0109819 A1 | 6/2003 | Tsuruda et al. | |
| 2003/0125654 A1 | 7/2003 | Malik | |
| 2003/0175824 A1 | 9/2003 | Pishko et al. | |
| 2003/0225355 A1 | 12/2003 | Butler | |
| 2004/0001879 A1 | 1/2004 | Guo et al. | |
| 2004/0060867 A1 | 4/2004 | Kriksunov et al. | |
| 2004/0120849 A1 | 6/2004 | Stewart et al. | |
| 2004/0142041 A1 | 7/2004 | MacDonald et al. | |
| 2004/0162512 A1 | 8/2004 | Liedtke et al. | |
| 2004/0220505 A1 | 11/2004 | Worthley | |
| 2005/0015036 A1 | 1/2005 | Lutri et al. | |
| 2005/0043820 A1 | 2/2005 | Browning | |
| 2005/0085757 A1 | 4/2005 | Santanello | |
| 2005/0147457 A1 | 7/2005 | Badejo et al. | |
| 2005/0153090 A1 | 7/2005 | Marchitto et al. | |
| 2005/0154340 A1 | 7/2005 | Schlussel | |
| 2005/0182443 A1 * | 8/2005 | Jonn | A61B 17/00491 606/213 |
| 2005/0208100 A1 | 9/2005 | Weber et al. | |
| 2005/0288706 A1 | 12/2005 | Widomski et al. | |
| 2006/0058721 A1 | 3/2006 | Lebner et al. | |
| 2006/0141012 A1 | 6/2006 | Gingras | |
| 2006/0173394 A1 | 8/2006 | Stroock et al. | |
| 2006/0265005 A1 | 11/2006 | Beese | |
| 2007/0106195 A1 | 5/2007 | Marcoux et al. | |
| 2007/0218101 A1 | 9/2007 | Johnson et al. | |
| 2007/0272211 A1 | 11/2007 | Kassner | |
| 2007/0299542 A1 | 12/2007 | Mathisen et al. | |
| 2008/0051687 A1 | 2/2008 | Rogers | |
| 2008/0154168 A1 | 2/2008 | Lutri | |
| 2008/0086113 A1 | 4/2008 | Tenney et al. | |
| 2008/0109034 A1 | 5/2008 | Mather et al. | |
| 2008/0110961 A1 | 5/2008 | Voegele et al. | |
| 2008/0167633 A1 | 7/2008 | Vannucci | |
| 2008/0280037 A1 | 11/2008 | Sheridan et al. | |
| 2008/0302487 A1 | 12/2008 | Goodman et al. | |
| 2009/0074842 A1 | 3/2009 | Hsu | |
| 2010/0106120 A1 | 4/2010 | Holm | |
| 2010/0262091 A1 | 10/2010 | Larsson | |
| 2010/0298791 A1 | 11/2010 | Jones et al. | |
| 2011/0047766 A1 | 3/2011 | McAulay et al. | |
| 2011/0071415 A1 | 3/2011 | Karwoski et al. | |
| 2011/0092874 A1 | 4/2011 | Baschnagel | |
| 2011/0208102 A1 | 8/2011 | Chawki | |
| 2011/0253303 A1 | 10/2011 | Miyachi et al. | |
| 2012/0179176 A1 * | 7/2012 | Wilson | A61L 31/10 606/151 |
| 2012/0220912 A1 | 8/2012 | Shang | |
| 2012/0238933 A1 | 9/2012 | Murphy et al. | |
| 2012/0277645 A1 | 11/2012 | Kikuta et al. | |
| 2013/0012988 A1 | 1/2013 | Blume et al. | |
| 2013/0041337 A1 | 2/2013 | Aali et al. | |
| 2013/0066365 A1 | 3/2013 | Belson et al. | |
| 2013/0084323 A1 | 4/2013 | Riebman et al. | |
| 2013/0138068 A1 | 5/2013 | Hu et al. | |
| 2013/0143326 A1 | 6/2013 | Tai et al. | |
| 2013/0144399 A1 | 6/2013 | Tai et al. | |
| 2013/0204077 A1 | 8/2013 | Nagale et al. | |
| 2013/0218125 A1 | 8/2013 | Stopek et al. | |
| 2013/0245784 A1 | 9/2013 | Tan et al. | |
| 2013/0274717 A1 | 10/2013 | Dunn | |
| 2013/0282049 A1 | 10/2013 | Peterson et al. | |
| 2013/0317405 A1 | 11/2013 | Ha et al. | |
| 2014/0024989 A1 | 1/2014 | Ueda | |
| 2014/0107561 A1 | 4/2014 | Dorian et al. | |
| 2014/0121649 A1 | 5/2014 | Calco | |
| 2014/0155916 A1 | 6/2014 | Hodgkinson et al. | |
| 2014/0171888 A1 | 6/2014 | Croizat et al. | |
| 2014/0257348 A1 | 9/2014 | Priewe et al. | |
| 2014/0257517 A1 | 9/2014 | Deichmann et al. | |
| 2015/0057491 A1 | 2/2015 | Goddard et al. | |
| 2015/0209186 A1 | 7/2015 | Abbott et al. | |
| 2015/0257938 A1 | 9/2015 | Pensier | |
| 2015/0297413 A1 | 10/2015 | Blanco | |
| 2015/0314114 A1 | 11/2015 | La Rosa | |
| 2015/0351767 A1 | 12/2015 | Zoll et al. | |
| 2016/0030248 A1 | 2/2016 | Potters | |
| 2016/0089145 A1 | 3/2016 | Quintero et al. | |
| 2016/0296673 A1 | 10/2016 | Sambusseti | |
| 2017/0056568 A1 | 3/2017 | Shelton, IV et al. | |
| 2017/0056569 A1 | 3/2017 | Vendely et al. | |
| 2017/0189159 A1 | 7/2017 | Bartee et al. | |
| 2017/0273837 A1 | 9/2017 | Brueckner | |
| 2017/0367806 A1 | 12/2017 | Gingras et al. | |
| 2018/0085103 A1 | 3/2018 | Quintero et al. | |
| 2018/0085259 A1 | 3/2018 | Quintero | |
| 2018/0085260 A1 | 3/2018 | Quintero | |

FOREIGN PATENT DOCUMENTS

| | | |
|---|---|---|
| CN | 102781433 A | 11/2012 |
| CN | 203234898 | 10/2013 |
| EP | 0532275 | 3/1993 |
| EP | 0730874 | 9/1996 |
| EP | 0746293 A1 | 12/1996 |
| EP | 1161212 | 8/2000 |
| EP | 2359782 | 8/2011 |
| EP | 2377498 | 10/2011 |
| EP | 2805698 | 11/2014 |
| GB | 2078763 | 1/1982 |
| JP | 58-124123 U | 8/1983 |
| JP | 61-203020 | 12/1986 |
| JP | 62-87624 | 6/1987 |
| JP | 01-265967 | 10/1988 |
| JP | 2-140948 | 11/1990 |
| JP | 7-016258 | 1/1995 |
| JP | 2001-265967 | 9/2001 |
| JP | 1130927 S | 11/2001 |
| JP | 2002-537068 | 11/2002 |
| JP | 2003-153949 | 5/2003 |
| JP | 2004-24905 A | 1/2004 |

(56) References Cited

FOREIGN PATENT DOCUMENTS

| | | |
|---|---|---|
| JP | 2006-061263 | 3/2006 |
| JP | 2009-022730 | 2/2009 |
| JP | 1359502 S | 5/2009 |
| JP | 2011-004850 | 1/2011 |
| JP | 1571238 S | 3/2017 |
| JP | 1629290 | 4/2019 |
| WO | WO 1983/002586 | 8/1983 |
| WO | WO 1995/004511 | 2/1995 |
| WO | WO 1996/040797 | 12/1996 |
| WO | WO 1998/026719 | 6/1998 |
| WO | WO 2000/049983 | 8/2000 |
| WO | WO 2004/049987 | 6/2004 |
| WO | 2005/007022 A2 | 1/2005 |
| WO | WO 2005/051259 | 6/2005 |
| WO | WO 2005/079674 | 9/2005 |
| WO | WO 2006/017109 | 2/2006 |
| WO | WO 2008/082444 | 7/2008 |
| WO | WO 2009/067062 | 5/2009 |
| WO | WO 2010/134873 | 11/2010 |
| WO | WO 2013/009725 | 1/2013 |
| WO | WO 2014/083570 | 6/2014 |
| WO | WO 2014/195710 | 12/2014 |
| WO | WO 2015/135351 | 9/2015 |

OTHER PUBLICATIONS

JP 3059327, 1991, English claims.
Japanese Office Action dated Feb. 19, 2019 for Design Appln. No. 2018-017274.
Japanese Office Action dated Feb. 26, 2019 for Patent Appln. No. 515463.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
3M™ Steri-Strip Adhesive Closures Product Catalog Brochure, (2011) 4 pages.
3M™ Steri-Strip Adhesive Closures Product Catalog Brochure, (2011) 8 pages.
3M™ Steri-Strip Adhesive Closures Product Catalog Brochure, (2012) 12 pages.
Allen, L.V. Jr et al Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.
Ashley et al.: Further studies involving wound closure with a rapidly polymerizing adhesive; *Plastic and Reconstructive Surgery;* Apr. 1963; vol. 31; pp. 333-343.
Ashley et al.: Nonsutured closure of skin lacerations and nonsutured grafting of skin with a rapidly polymerizing adhesive; *Qtrly Bull. Northwestern University (Evanston, Ill.) Medical School;* 1962; vol. 36; pp. 189-194.
Brombeg et al.: Nonsuture fixation of split-thickness skin grafts; *Surgery,* Jun. 1964; vol. 55; pp. 846-853.
Cramer: Rapid Skin Grafting in Small Animals; *Plastic and Reconstructive Surgery and the Transplantation Bull;* Oct. 1962, vol. 30; pp. 149-150.

Cramer et al.: Autograft rejection induced by homografting. A phenomenon intermediate between homograft rejection and autoimmunity; *Plastic and Reconstructive Surgery;* Jun. 1965; vol. 35; pp. 572-587.
DeMaria, E. 'New skin closure system facilitates wound healing after cardiovascular implantable electronic device surgery' World Journal of Clinical Cases (2015) 3(8) pp. 675-677.
Dermabond Prineo Skin Closure Systems (22 cm) Brochure (2014), 7 pages.
Dermabond Prineo Skin Closure Systems (22 cm) Brochure (2015), 2 pages.
Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).
Inou: Studies on the Surgical Use of Plastic Adhesive; *Am. Journal of Proctology;* 1962; vol. 13; pp. 219-226.
Jesse et al.: Fixation of split-thickness skin grafts with adhesive; *Plastic and Reconstructive Surgery;* Mar. 1964; vol. 33; pp. 272-277.
Kaplan: A technique of nonsuture wound closure with a plastic tissue adhesive; *Plastic and Reconstructive Surgery;* Feb. 1966; vol. 37(2); pp. 139-142.
Keddie et al.: Intrafollicular tinea versicolor demonstrated on monomer plastic strips; *Journal of Investigative Dermatology;* Sep. 1963; vol. 41; pp. 103-106.
Lazar, H.L. et al 'Novel Adhesive Skin Closures Improve Wound Healing Following Saphenous Vein Harvesting' J. Card Surg (2008) 23 pp. 152-155.
Leukosan SkinLink Application Guide (2006) 1 page.
Leukosan Skinlink. Bsn Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.
Pam Marketing Nut. Yikes! The Social Medica Quick Fix Band-Aids are Falling Off! Jul. 2012 [earliest online date], [site visited May 8, 2018]. Available from Internet,,URL:http://www.pammarketingnut.com/2012/07/yikes-the-social-media-quick-fix-band-aids-are-falling-off/> (Year: 2012).
Parrish et al.: Synthetic resin adhesive for placement of skin grafts; *American Surgeon;* Nov. 1964; vol. 30; pp. 753-755.
Raekallio et al.: Acute reaction to arterial adhesive in healing skin wounds; *Journal of Surgical Research;* Mar. 1964; vol. 4; pp. 124-127.
Stone: Nonsuture closure of cutaneous lacerations, skin grafting and bowel anastomosis; *American Surgeon;* Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M. et al 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wang et al 'Biodegradable microfluidic scaffolds for tissue engineering from amino alcohol-based poly(ester amide) elastomers' Organogenesis (2010) 6:4, pp. 212-216.
Wolfe et al.: The application of hydrostatic pressure to the burn injury, an experimental study: *Journal of Trauma: Injury Infections & critical Care;* May 1962; vol. 2; pp. 262-272.
ZipLine medical Zip Surgical Skin Closure Brochure (2013) 4 pages.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.

(56) References Cited

OTHER PUBLICATIONS

Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
Corrected International Search Report International Application No. PCT/US2005/004948 dated Jun. 22, 2005.
Extended European Search Report re: 14166813.7 dated Jul. 7, 2014.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
International Preliminary Report on Patentability for International Application No. PCT/US2005/024042 dated Jan. 16, 2007.
International Search Report for International Application No. PCT/US2005/004948 dated Jun. 22, 2005.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.
U.S. Appl. No. 09/919,877, filed Aug. 2, 2001.
U.S. Appl. No. 10/779,721, filed Feb. 18, 2004.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.

\* cited by examiner

SKIN CLOSURE DEVICES WITH INTERRUPTED CLOSURE

The present disclosure relates to skin closure devices applied over a surgical incision and preferably secured by a polymerizable adhesive, with the devices capable of forming drainage openings and absorbent flaps for removal of wound exudates and wound inspection.

BACKGROUND

A number of devices and methods exist for closing skin or tissue having a surgical incision, opening, cut, wound, or dissection. With these devices, skin or tissue parts separated by the incision are approximated or brought into close proximity forming as narrow a gap as possible in the area of the surgical incision or cut, and then covered by an adhesively attached tape which holds the skin or tissue in closed apposed arrangement until wound healing occurs after which the tape is removed.

Commercially available DERMABOND® PRINEO® Skin Closure System comprises a mesh having a pressure sensitive adhesive and a polymerization initiator disposed on the mesh. The mesh is applied onto the skin over a wound, and a polymerizable cyanoacrylate-based adhesive is then applied on the mesh and bonds the mesh to the skin.

PCT Publication WO2014/195710, SUTURELESS WOUND CLOSURE, discloses a sutureless wound closure device comprising: a) a base layer for attaching the device to skin; and b) an upper tensioning layer having a first end anchored to the base layer and a second, opposite end including fixing means to attach the end to the base layer, wherein the base layer includes an aperture that, in use, is covered by the upper tensioning layer.

U.S. Pat. No. 8,603,053, PRIMARY DRESSING, discloses a liquid-permeable primary dressing (100) in the form of a flexible thermoplastic material section (1.1; 1.2; 1.3; 1.4; 1.5), comprising: a first surface (4) of the material section (1.1; 1.2; 1.3; 1.4; 1.5), a second surface (5) of the material section (1.1; 1.2; 1.3; 1.4; 1.5) facing away from the first surface (4), a plurality of three-dimensional perforations (2; 2"; 21) whose walls (3), starting from the first surface (4), run out into an edge projection with a free edge (8) and impart a rough grip to the second surface (5), characterized in that at least one of the free edges (8) merges into a section (12) bent approximately vertically to a perforation axis (A), the first surface is smooth, and each free edge is substantially equidistant from the first surface.

European Patent Application Publication No. EP0730874A2, CLOSURE TAPE FOR IMPROVED WOUND OR INCISION HEALING AND ITS USE, discloses use of a tape comprising: (i) a polymeric elastic film that is substantially impermeant to microorganisms, and (ii) a hydrocolloid adhesive coating on one face of the film and having fluid absorbing capacity, for the manufacture of a closure tape for use in closing a breach of the skin of the type that has typically been closed with sutures.

U.S. Pat. No. 5,308,313, VENTED WOUND DRESSING, discloses a vented wound dressing comprising a thin conformable sheet material a portion of which is adopted for placement as a dressing covering a wound and skin surrounding the wound. The dressing has a periphery defined by opposed edges of the sheet material, the sheet material having opposed surfaces, one of the surfaces carrying a layer of a pressure-sensitive adhesive, the adhesive in that portion for placement on the wound being applied to provide repeating spaced areas containing no adhesive. At least a portion of only the repeating areas of the sheet material containing no adhesive having slits extending through the opposed surfaces of the sheet material to permit transfer of wound fluids through the sheet material purportedly unimpeded by a presence of adhesive material which can clog the slits and thereby inhibit fluid transfer therethrough. Each of the slits having smaller dimensions than the repeating areas of the sheet material containing no adhesive whereby each slit occupies only a portion of the area containing no adhesive having a slit. The dimensions and number of the slits is described as being such as to retain sufficient moisture to provide a moist healing wound dressing. The adhesive around the periphery of the sheet material being present as a continuous layer uninterrupted by repeating areas containing no adhesive for securing the dressing to skin. The continuous peripheral layer of adhesive defines the portion of the sheet material adapted for placement on a wound, the continuous peripheral layer of adhesive further maintaining a barrier function against bacteria and other external contaminants as well as helping to ensure that no wound fluids escape laterally.

U.S. Pat. No. 5,106,362, Vented Absorbent Dressing, discloses a dressing for a wound of a patient, comprising: a base sheet for contacting the skin of the patient, said base sheet having an opening for placement over the wound, and means for securing the base sheet to the skin of a patient; and vent means for providing controlled leakage of fluid along a tortuous path from the wound through the opening of the base sheet. The vent means comprises a sheet material secured to said base sheet and covering said opening, said sheet material purported to reduce evaporation through said opening while controlling said leakage of fluid along a tortuous path, purportedly helping to insure a moist environment for said wound.

U.S. Patent Application Publication No. 20140024989, WOUND DRESSING, discloses a wound dressing comprising: a perforated material including through-holes; and a low-adhesive resin coating at least one face of the perforated material without closing the through-holes; wherein the perforated material is a knitted fabric or a woven fabric formed of a multifilament, and the perforated material has an average opening area of the through-holes of 0.02 to 1.2 $mm^2$ and an average number of through-holes of 40 to 220 $cm^2$.

U.S. Patent Application Publication No. 20130317405, MODULAR WOUND DRESSING, describes a medical dressing comprising two backing layers. In particular, the two backing layers are in overlapping relation to one another and entirely surround an opening to form a window.

U.S. Pat. No. 9,000,251, Draining Wound Dressing, discloses a medical dressing made of multiple layers and includes a collection chamber that is in fluid communication with a drainage channel.

U.S. Pat. No. 6,787,682, Absorbent Foam Wound Dressing, discloses a wound dressing comprising a foam layer of soft, hydrophilic polymeric foam having bodyside and backside surfaces, A base layer of elastomeric film is adhered to said bodyside surface of said foam layer; said base layer having at least one generally centrally located opening therein exposing said foam layer through said opening and having a bodyside surface coated with a hypoallergenic pressure-sensitive adhesive for adhesively contacting wound and surrounding skin surfaces at a wound site. A vapor-permeable liquid-impermeable elastomeric backing layer extends over said backside surface of said foam layer and said backing layer being unattached to said backside surface of said foam layer over said centrally located opening of said base layer.

U.S. Pat. No. 5,662,599, Disposable Wound Dressing and Support Unit, discloses a disposable wound dressing and support unit for holding a gauze pad in place on top of a wound and providing for access to the wound. The unit is purportedly adaptable for conforming to various parts of the anatomy of a patient and comprises: an elongated wrap having a top and a bottom, said wrap having a window opening therethrough, said window opening adapted for receipt above and on top of the gauze pad disposed on top of the wound. Fastener means is disposed on the bottom of said wrap and along a side of said window opening for permanently engaging a portion of the gauze pad. Securing means is attached to a first end portion of said wrap for engaging a portion of said wrap at any desired location along its length and securing said wrap on the patient.

U.S. Pat. No. 5,456,660, Wound Dressing Support Device, discloses a reusable wound dressing support device for holding a gauze pad in place on top of a wound and providing for access to the wound. The device is purportedly adaptable for conforming to various parts of the anatomy of a patient and comprises: an elongated wrap having a top and a bottom, said wrap having a window opening therethrough, said window opening adapted for receipt above and on top of the gauze pad disposed on top of the wound. A non-adhesive fastener means is disposed on the bottom of said wrap and along at least one side of said window opening for releasably engaging a portion of the gauze pad. Securing means are attached to opposite ends of said wrap for securing said wrap on the patient.

PCT Publication WO2015135351A1, LIQUID-ABSORPTION WOUND DRESSING HELPING TO OBSERVE WOUND SURFACE, discloses a liquid-absorbent wound dressing characterized in that it comprises a sheet-like liquid absorbent material.

U.S. Patent Application Publication No. 20150314114, COLLAGEN DEVICE, discloses a device adapted for dressing and treating wounds, skin lesions/ulcers, sores and burns, comprising at least one biocompatible membrane and at least one catheter coupled to said membrane.

U.S. Patent Application Publication No. 20140121649, WOUND DRESSING ASSEMBLY WITH ABSORBENT LAYER, discloses a surgical wound dressing assembly for a surgical tube wound or other device entrance into the body, comprising: a cover layer, with adhesive on the outer perimeter of the underside of the cover layer; an absorbent ring secured to the underside of the cover; an interior clear window allowing the nurse or other medical personnel to view the wound site through the window for inspection for infection or bleeding; and a port formed in the window area to allow a tube or other device to pass through the wound dressing.

U.S. Pat. No. 6,245,960, Inherent Healing Accelerator, discloses a dressing for open wounds, comprising an elastomer sheet having a plurality of fenestrations, wherein said fenestrations comprise openings penetrating through said elastomer sheet whereby granulation tissue may grow from the open wound through said fenestrations so as to substantially cover said elastomer sheet; wherein each of said fenestrations comprise a maximum dimension of around 4 millimeters to around 6 millimeters.

U.S. Pat. No. 4,795,435, Device for Protecting a Wound, discloses a device for protecting a wound comprising a pad of skin-protective and skin-curative adhesive material having secured thereto a foldable sheet of liquid impermeable material of larger area than the pad, marginal portions of said foldable sheet provided with a layer of pressure-sensitive adhesive, and said sheet folded over itself and sealed in liquid-tight fashion around its edges to define a compartment whereby the marginal portions can be manually pulled apart if desired.

U.S. Pat. No. 5,449,340, Bandage for Replaceable Dressing, discloses a bandage for retraining a dressing against a patient's skin comprising a tape having an adhesive inner layer surface with pressure sensitive adhesive thereon and a non-adhesive outer surface. The tape further comprising a base portion including said inner surface for adhesive securement to said patient's skin, opening means in said base portion for placement over a wound on said patient's skin for receiving a dressing when said base portion is secured to said patient's skin and tab means for overlying said opening means. The tab means is formed from said tape being bent back on itself with said adhesive inner surface secured in a face-to-face relationship, an exposed portion of said inner adhesive surface on said tab means, said exposed portion of said inner adhesive surface being located so that it is in facing relationship to said opening means in said base portion and pad means adhesively secured to said exposed portion of said inner adhesive surface of said tab means for overlying said opening means and securing means for securing facing portions of said tab means and said outer surface of said base portion containing said opening means to each other to secure said tab means to said base portion with said pad means located in said opening means and position between said tab means and said patient's skin.

PCT Publication WO1995004511. IMPROVEMENTS IN AND RELATING TO DRESSINGS, discloses a dressing comprising a skin patch having a top and bottom surface, said bottom surface having an adhesive area; a cover flap attached to said skin patch, the attachment allowing the cover flap to be positioned over at least a portion of the top surface of said skin flap; said dressing including fastening means for holding the cover flap over the top surface of said skin patch.

U.S. Pat. No. 5,086,763, Protective Reclosable Wound Dressing, discloses a disposable, protective, reclosable wound dressing bandage providing access to a wound. The dressing comprising: an adhesive tape for adhering said bandage to a body part, said tape having an opening such that the wound is circumscribed therein; a soft pad frame affixed to said adhesive tape and said soft pad frame having an opening in registry with said opening in said adhesive tape, said soft pad frame providing an outward offset from said adhesive tape; a pad frame secured to said soft pad frame, said pad frame having an opening in registry with said openings in said adhesive tape and in said soft pad frame, respectively, said pad frame being fabricated from a fabric used to adhere to a micro hook material; a gauze pad having dimensions such that said gauze pad fits within said openings in registry with said adhesive tape, said soft pad frame and said pad frame; a removable inspection, medication covering flap having micro hook material on a substantial portion of a side thereof for detachably securing said flap to said pad frame and to said gauze pad, said flap having a tab for use by a care provider so as to open, close and remove said flap.

However, skin closure systems may benefit from means to enable removal and drainage of wound exudates for wounds closed using skin closure systems, when required. Because skin closure systems seal the wound tightly, it can be beneficial to relieve any exudate pressure buildup or minimize the onset of skin maceration when the amount of exudates is significant.

Skin closure devices and dressings having porated or porous or apertured tape structure can release the pressure of wound exudates and provide for drainage, however these systems will also leave the incision and wound open to ingress of contaminates through the pores or apertures, potentially resulting in infection. There continues to be a need for improved devices, systems, and methods for holding skin areas around the dissection in apposed arrangement and covered and isolated from ingress of contaminants, while still providing for drainage of exudates and capability to non-disruptively inspect the wound conditions under the wound closure device

SUMMARY OF THE INVENTION

In one embodiment, the invention relates to a device for application onto incisions or wounds with a liquid rapidly polymerizable adhesive for forming skin closure systems, comprising a device for application onto incisions or wounds with a liquid rapidly polymerizable adhesive for forming skin closure systems, comprising a flat porous mesh elongated along a longitudinal axis and having an upper side and an opposing lower or wound facing side and a central portion in immediate vicinity of the axis; further having a plurality of pores and windows in said mesh, said windows substantially larger than said pores and arranged along said longitudinal axis in said central portion; a crosslinking or polymerization accelerator or initiator disposed in or on said mesh; and a pressure sensitive adhesive disposed on at least a portion of the lower surface of said mesh.

In some embodiments, there is provided a flat cover attached to said mesh at an edge of said mesh; said cover configured to be foldable over the upper side of said mesh in a book-like fashion and sized to as least partially cover said mesh and to fully cover said windows.

In some embodiments, there are provided absorbent pads attached to said mesh at the edge of said mesh and sized to cover said windows, said absorbent pads disposed in a book-like arrangement between said flap and said mesh and foldable over the upper side of said mesh.

In some embodiments, there is provided a mask comprising an elongated, flexible, flat strip comprising a plurality of masking segments arranged along said strip and interconnected by narrow connectors; said mask having a mesh-facing surface and an opposing top surface; said masking segments configured and sized to completely cover said windows when the mask is disposed on the mesh; with spacing between masking segments matching corresponding spacing between windows with the masking segments in registration over the windows; said mask further comprising a lift-up tab linearly extending at one end of the mask; said mask removably attached with mesh-facing surface onto the upper side of the mesh with the masking segments covering the windows.

According to another embodiment, a method is provided of using the device for application onto incisions or wounds with a liquid rapidly polymerizable adhesive for forming skin closure systems on a wound for skin incision closure, comprising the steps: positioning the device with the lower side facing the wound; orienting the axis in alignment with the incision ensuring the axis is approximately overlapping the incision; approximating edges of the incision to each other with the device and adhering the device to the skin; applying a polymerizable adhesive onto the upper side of the mesh but not through the windows, allowing the adhesive to penetrate through the mesh and contact the skin; allowing the adhesive to react with the initiator or accelerator of polymerization and polymerize thus bonding the mesh to the skin; folding said cover over the upper side of said mesh in a book-like fashion and at least partially covering said mesh and fully covering said windows. The methods can further comprise the steps of applying a polymerizable adhesive onto the upper side of the mesh and the top surface of the mask; allowing the adhesive to penetrate through the mesh and contact the skin; allowing the adhesive to react with the initiator or accelerator of polymerization and at least partially polymerize thus bonding the mesh to the skin; peeling off the mask from the mesh.

DETAILED DESCRIPTION

Embodiments with Windows

Figure 1A:
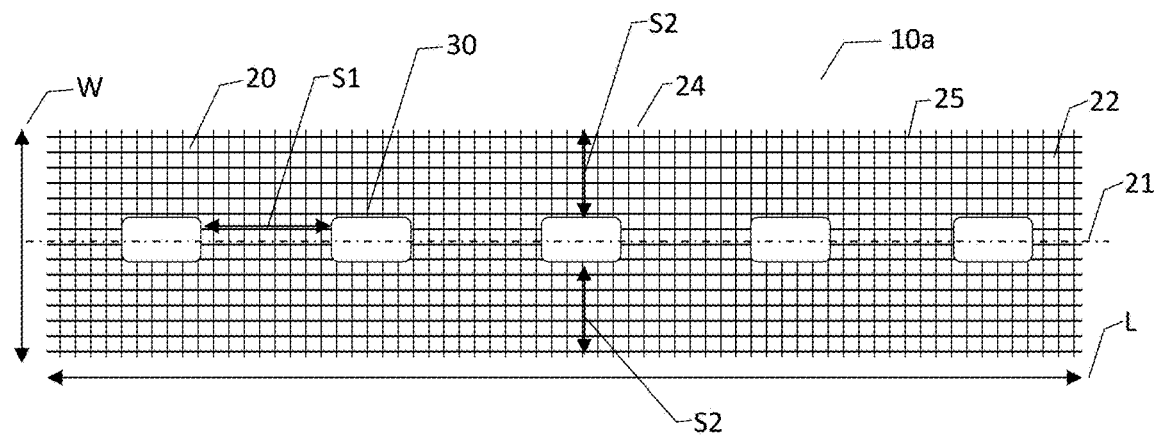
FIGS. 1a, 1b, 1e show embodiments of the skin closure device in a schematic view from an upper side.
Figure 1B:
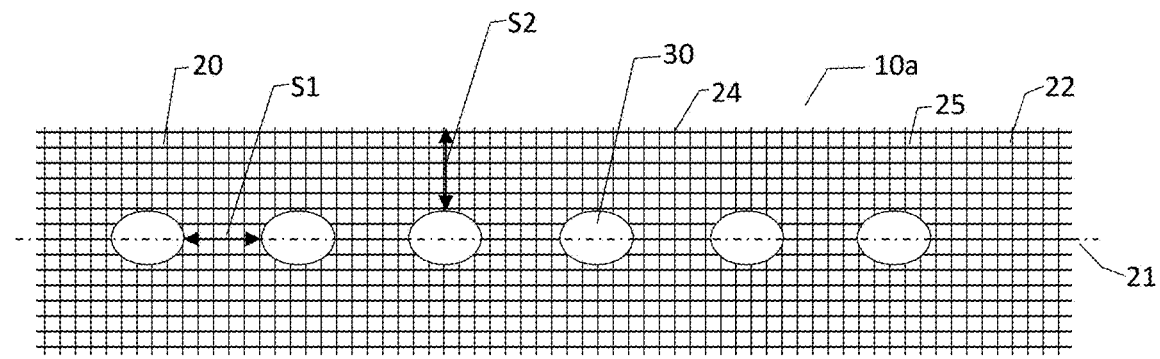

Referring now to FIGS. 1a, 1b, embodiments of skin closure system device 10a are shown in a schematic view from an upper side 22, with device 10a comprising a thin, flat, flexible mesh 20 having length L and width W and elongated along longitudinal axis 21, with upper side 22 and lower side 23. Mesh 20 comprises a porous tape having, perforations or micro-holes 25 throughout and can be a woven, non-woven, extruded, punched, perforated, molded, etc. substrate. Mesh 20 is coated and/or impregnated with an initiator or accelerator of polymerization. Perforations or micro-holes 25 are openings that can be of any shape, including rectangular, triangular, elliptical, etc. When round, perforations 25 have diameters from about 0.2 mm to about 2 mm, such as 0.5, 1, 1.5 mm. When square, the side of perforations 25 is from about 0.2 mm to about 2 mm, such as 0.5, 1, 1.5 mm. Area of individual perforations 25 is from about 0.04 mm2 to about 4 mm2. Mesh 20 has from 25% to 80% taken by perforations 25.

Mesh 20 has a plurality of large openings or large apertures or windows 30, generally arranged in a central portion of mesh 20 along longitudinal axis 21. Windows 30 are sized to be much larger than perforations 25, such as at least 10 times larger (by area) such as 10, 15, 20, 30, 50, 100, 200, 500, 1000 times larger. Windows 30 can be of any shape, including rectangular, triangular, elliptical, etc., with rectangular windows 30 shown in FIG. 1a, and elliptical windows 30 shown in FIG. 1b. When round, windows 30 have diameters from about 3 mm to about 15 mm, such as 4, 5, 10, 12 mm. When square, the side of windows 30 is from about 3 mm to about 15 mm, such as 4, 6, 8, 10, 12 mm. Area of individual windows 30 is from about 9 mm2 to about 225 mm2. Windows 30 are arranged generally uniformly along longitudinal axis 21, with from 1 to 4 windows 30 per 5 cm length of axis 21. In some embodiments, distance S1 between windows 30 is from about 10 mm to about 30 mm such as 12, 15, 20, 25 mm. In some embodiments, distance S2 between windows 30 and mesh 20 edge 24 is from about 5 mm to about 30 mm such as 7, 10, 15, 20 mm.

Figure 1C:
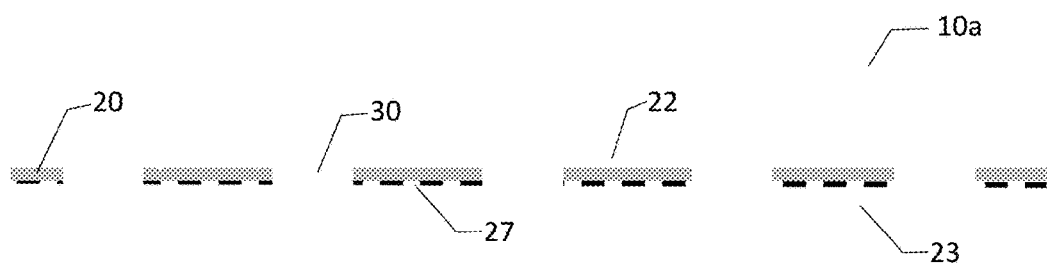
FIG. 1c shows an embodiment of the skin closure device in a schematic side cross-sectional view.
Figure 1D:
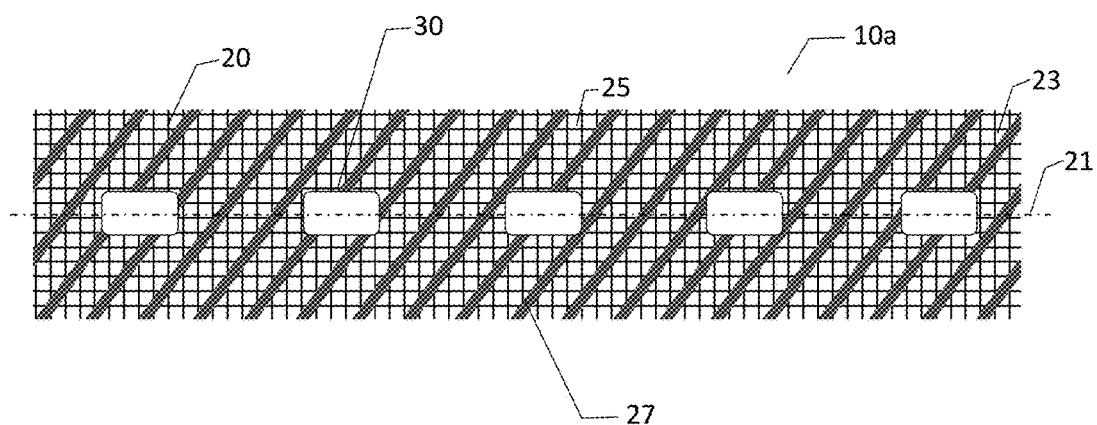
FIG. 1d shows an embodiment of the skin closure device in a schematic view from lower side.

Further reference is made to FIG. 1c and FIG. 1d. FIG. 1c shows a schematic side cross-sectional view of skin closure system device 10a, with cross-section taken along axis 21 to show windows 30. FIG. 1d shows a schematic view of device 10a from lower side 23. On lower side 23, which is tissue or skin facing side in use of device 10a, there is a plurality of elongated traces 27 of pressure sensitive adhesive (PSA), said traces covering from 3% to about 60% of area of mesh 20, more preferably 5% to 50%, such as 5%, 10%, 20%, 40%. Traces 27 can be in a form of linear segments of PSA (as shown) and can run under any angle to axis 21, such as under angle of about 45° as shown. Traces 27 can have any non-linear shape as well such as round, square, elliptical PSA dots (not shown) or similar.

Figure 1E:
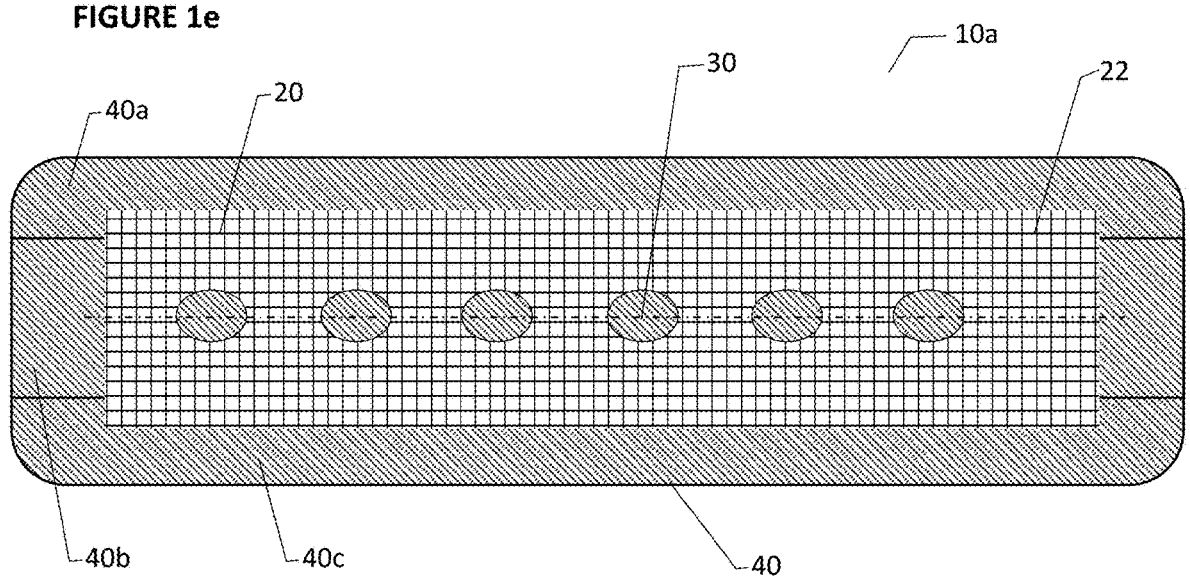

Referring now to FIG. 1e, showing a view from upper side 22 similar to FIGS. 1a, 1b, on lower side 23, an optional easy-to-peel off liner 40 can be disposed extending at least over all lower side 23 of mesh 20 and covering all lower side 23 of mesh 20 to protect traces 27 of pressure sensitive adhesive (PSA). Liner materials are known in the art and are typically made of synthetic or natural polymers that are easily peelable from PSA. Liner 40 can be one piece (not shown) or can comprise 2, 3, 4, or more segments. As shown in FIG. 1e, liner 40 comprises 3 segments, with central segment 40b sandwiched between peripheral segments 40a and 40c.

Figure 1F:
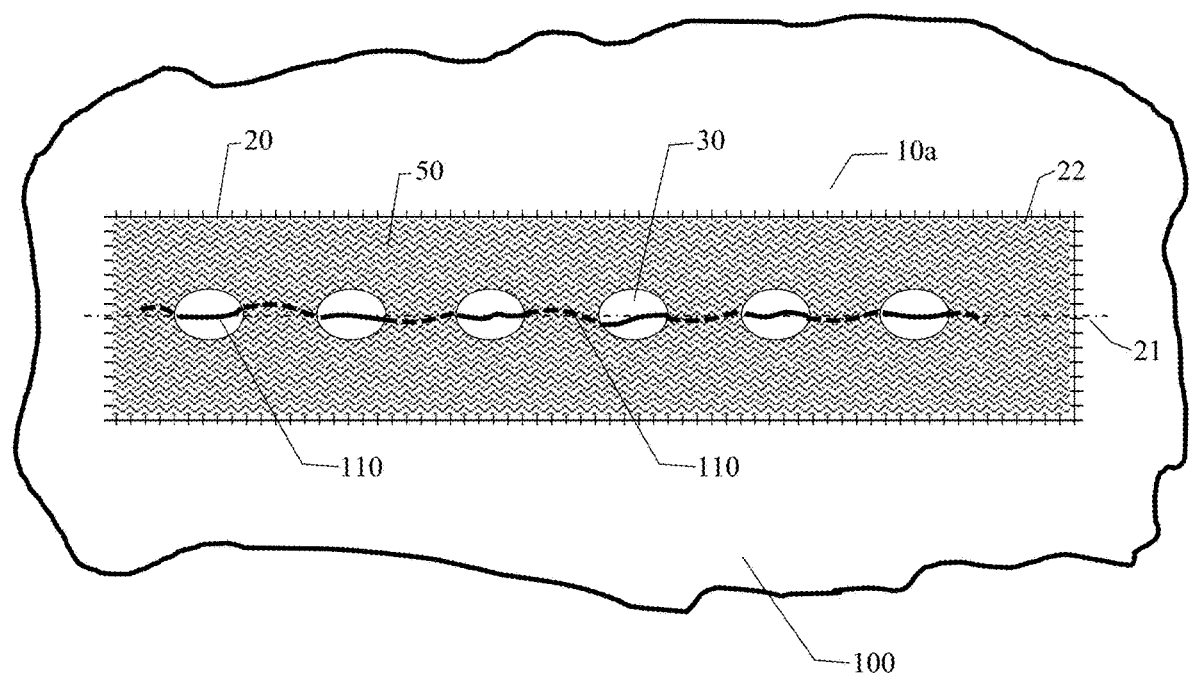
FIG. 1f shows an embodiment of the skin closure device disposed on a wound in a schematic view from an upper side.

In use, and further referring to FIG. 1f, mesh 20, shown in the top view from upper side 22, after removal of optional liner 40 material covering lower side 23, is positioned on tissue or skin 100 covering wound 110 with lower side 23 facing the wound 110 and upper side 22 facing away from the wound 110. Mesh 20 is secured to wound surface 100 (such as skin) by traces 27 of PSA. Optionally, mesh 20 is used to approximate and hold in apposition or close approximation the edges of surgical incision or wound 110, using traces 27 of PSA for securement of mesh 20 and for securing in close approximation or apposition the edges of surgical incision or wound 110.

Generally longitudinal axis 21 is aligned and superimposed over the wound 110. The positioning of device 10 over the surgical incision or wound 110 is performed so that axis 21 is as much as possible aligned with the surgical incision or wound 110 and overlaps with the surgical incision or wound 110 i.e., axis 21 is in registration the surgical incision or wound 110.

Polymerizable or cross-linkable adhesive 50 (not shown) is then uniformly applied over the whole of mesh 20 upper surface 22, with the exception of windows 30, penetrating through mesh 20 and establishing contact with skin 100. Adhesive 50 is not applied on top of or through windows 30. Adhesive 50 can be expressed from a container having a porous tip impregnated with a polymerization or cross-linking accelerator or initiator. In a preferred embodiment, adhesive 50 is expressed from an applicator not having polymerization or cross-linking accelerator or initiator, with such polymerization or cross-linking accelerator or activator/initiator present on or in mesh 20 in a releasable or reactive form, i.e., available for rapid reaction when contacted with adhesive 50.

Liquid adhesive 50 then polymerizes and/or cross-links and solidifies, establishing secure bond with skin 100 and mesh 20. Skin closure by device 10a is thus completed with surgical incision under mesh 20 securely covered and closed, with windows 30 providing areas of wound 110 which are non-covered by adhesive 50, allowing for drainage, inspection, and access.

Embodiments with Windows and Flap or Cover

Figure 2A:
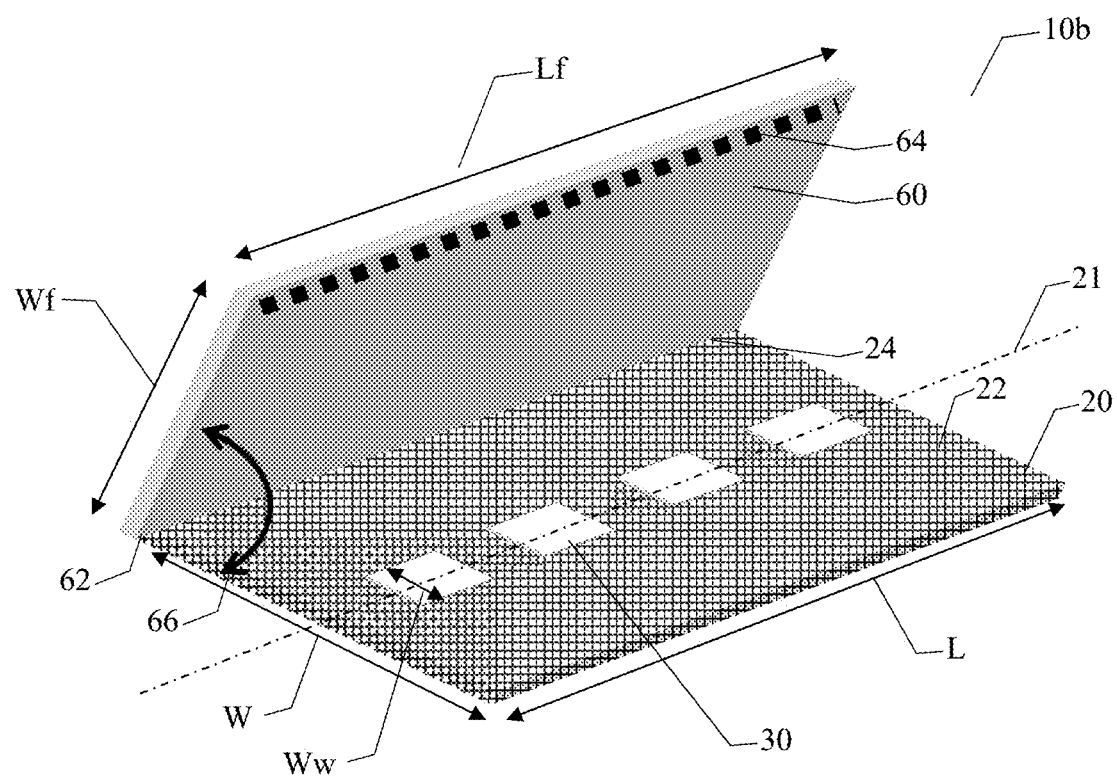
FIGS. 2a, 2b shows an embodiment of the skin closure device in a schematic perspective view.

Referring now to FIG. 2a, an embodiment of skin closure system device 10b is shown in a schematic perspective view, with device 10b comprising mesh 20 as described in embodiments of device 10a above, to which a flap or cover 60 is attached along long edge 24 forming a hinge 62 so that flap 60 can be opened (as shown) or closed covering mesh 20 in a book-like fashion on upper side 22. Arrow 66 illustrates opening and closing flap 60. Flap 60 is serving as a protector of wound exposed in windows 30, and it can be transparent or opaque. Flap 60 is sized close to size of mesh 20 that flap 60 will be covering, but flap 60 can be up to 25% larger or smaller (by area). In all embodiments, flap 60 is seized so as to at least cover all windows 30 when flap 60 is closed, i.e. when flap 60 is folded onto mesh 20. In some embodiments, flap 60 is sized to have the same length Lf as mesh 20 length L, but smaller flap width (Wf) than mesh 20 width W, sized so that flap 60 at least fully covers all windows 30 when flap 60 is closed. In one embodiment Wf is equal to one half of mesh 20 width W plus the diameter or width of window 30 (Ww), i.e. Wf=0.5*W+Ww, resulting in flap 60 fully covering the windows 30 when flap 60 is closed.

Flap 60 can have an optional PSA coating on a portion or on all surface of flap 60 facing mesh 20, in order to removably fixate flap 60 onto mesh 20 and protect wound areas visible in windows 30. After attachment by PSA, flap 60 can be lifted upwards for inspection of wound 110 and then reclosed as needed. Alternatively to PSA covering all surface of flap 60 facing mesh 20, flap 60 can have a PSA zone only on a portion of surface of flap 60 facing mesh 20, such as a narrow PSA strip 64 positioned alone the edge opposite edge 24 and hinge 62 as shown in FIG. 2a. Narrow PSA strip 64 can also optionally be covered by a peelable liner (not shown).

Flap or cover 60 provides covering preventing contamination of wound and tissue exposed in windows 30 and ingress of contaminants, infectious microorganisms, etc., while simultaneously allowing drainage, access and inspection. Flap 60 can be transparent for ease of inspection or opaque in which case flap 60 is lifted for inspection.

In use of device 10b, similarly to the above description of device 10a, after removal of optional liner 40 material covering lower side 23, device 10b is positioned on tissue or skin 100 covering wound 110 with lower side 23 facing the wound 110 and upper side 22 facing away from the wound 110. Mesh 20 is secured to wound surface 100 (such as skin) by traces 27 of PSA. Optionally, mesh 20 is used to approximate and hold in apposition or close approximation the edges of surgical incision or wound 110, using traces 27 of PSA for securement of mesh 20 and for securing in close approximation or apposition the edges of surgical incision or wound 110. Generally longitudinal axis 21 is aligned and superimposed over the wound 110.

Flap 60 is lifted up form contact with upper side 22 prior to application of adhesive 50 so as to not cover upper side 22 and windows 30 by flap 60. Polymerizable or cross-linkable adhesive 50 is then uniformly applied over the whole of mesh 20 upper surface 22, with the exception of windows 30, penetrating through mesh 20 and establishing contact with skin 100. Adhesive 50 is not applied on top of or through windows 30. Adhesive 50 can be expressed from a container having a porous tip impregnated with a polymerization or cross-linking accelerator or initiator. In a preferred embodiment, adhesive 50 is expressed from an applicator not having polymerization or cross-linking accelerator or initiator, with such polymerization or cross-linking accelerator or activator/initiator present on or in mesh 20 in a releasable or reactive form, i.e., available for rapid reaction when contacted with adhesive 50.

Liquid adhesive 50 then polymerizes and/or cross-links and solidifies, establishing secure bond with skin 100 and mesh 20. After full polymerization and/or cross-linking and solidifying of liquid adhesive 50, flap 60 is closed in a book-like fashion over upper side 22 covering upper side 22 and contacting upper side 22. Skin closure by device 10b is thus completed with surgical incision under mesh 20 securely covered and closed, with windows 30 providing areas of wound 110 which are non-covered by adhesive 50, allowing for drainage, inspection, and access, and windows 30 further covered and protected by openable flap 60.

Embodiments with Absorbent Insert

Figure 2B:
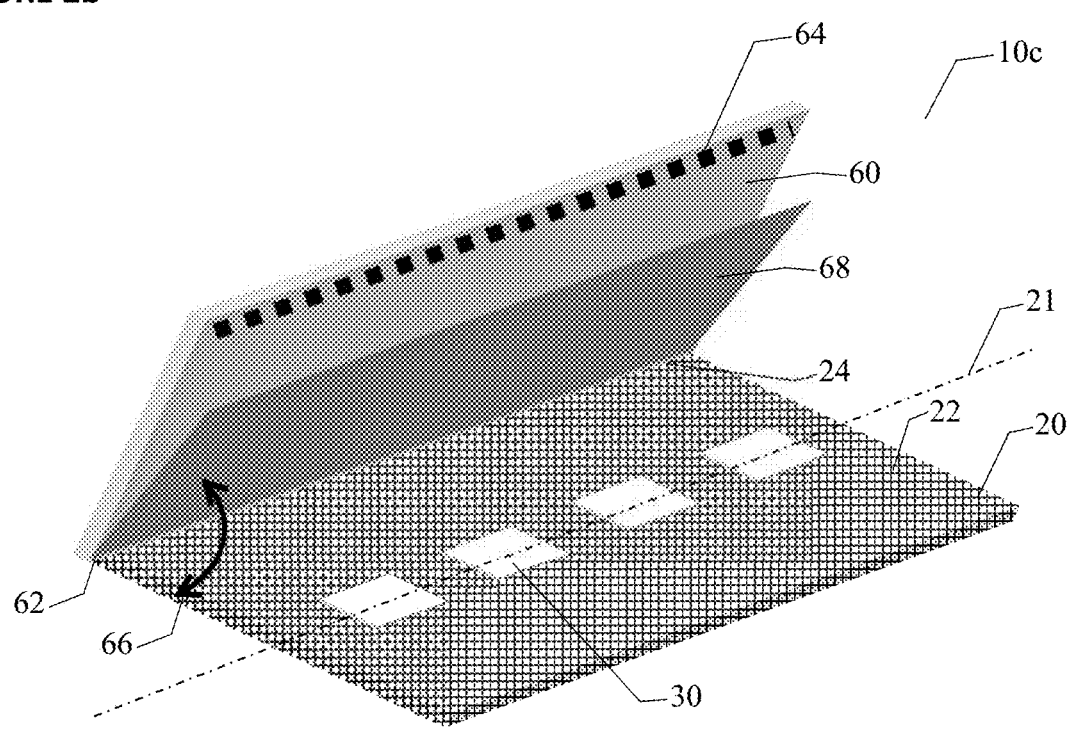

Referring now to FIG. 2b, an embodiment of skin closure system device 10c is shown in a schematic perspective view, with device 10c comprising mesh 20 and flap 60 as described above, whereby at least one and preferably more than one intermediate absorbent and removable insert 68 is attached between flap 60 and mesh 20 along long edge 24 forming the same hinge 62 so that insert 68 can be brought into contact with mesh 20 and covered by flap 60 in a book-like fashion. Arrow 66 illustrates opening and closing insert 68. Insert 68 is serving as an absorbent pad to absorb exudates draining from open windows 30, and it can be removed by tearing along edge 24, where insert 68 has optional perforated tear-out line (not shown). While one insert 68 is shown, there can be a plurality of inserts 38, such as 2, 3, 4, 5, 6, 7, 8, 10, most preferably 3-6. In use, as insert 68 closest to windows 30 has absorbed exudates, it is removed by tearing it out along edge 24, and flap 60 is closed again, covering next available insert 68.

Embodiments with Mask

Figure 3A:
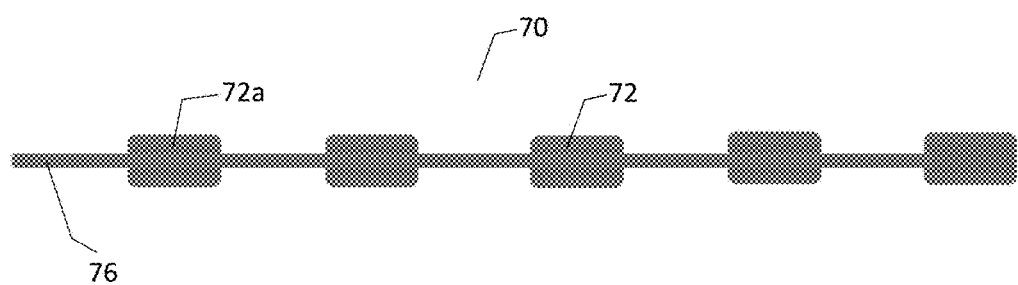
FIG. 3a shows an embodiment of the mask in a schematic top view.

In order to facilitate rapid and efficient application of polymerizable or cross-linkable adhesive 50 over the whole of mesh 20 upper surface 22 with the exception of windows 30, a sacrificial mask 70 is provided covering all windows 30 prior to application of adhesive 50. Referring now to FIG. 3a, mask 70 is shown in a top view, with mask 70 comprising an elongated, flexible, flat strip comprising masking segments 72 arranged along mask 70 and interconnected by connectors 74. A lift-up tab 76 linearly extending from masking segment 72a at one end of mask 70 (as shown), with an optional second lift-up tab (not shown) linearly extending from masking segment 72 on opposite end of mask 70.

Masking segments 72 configured and sized so as to completely cover windows 30 and are sized either exactly as windows 30, or more preferably are sized slightly larger than windows 30, such as extending outside of windows 30 or overlapping windows 30 on all sides by 0.25-2.5 mm on all sides, such as extending outside of windows 30 by 0.5, 1, 1.5, 2 mm on all sides. As an example, if window 30 is a rectangle 6 mm by 10 mm, masking segment 72 can be dimensioned as a rectangle 8 mm by 12 mm, thus extending 1 mm over and outside of window 30 when positioned in registration over window 30. Mask 70 is configured with spacing between masking segments 72 match corresponding spacing between windows 30. Mask 70 is configured to completely cover all windows 30 when mask 70 is positioned on top of mesh 20 with masking segments 72 in registration over windows 30.

Figure 3B:
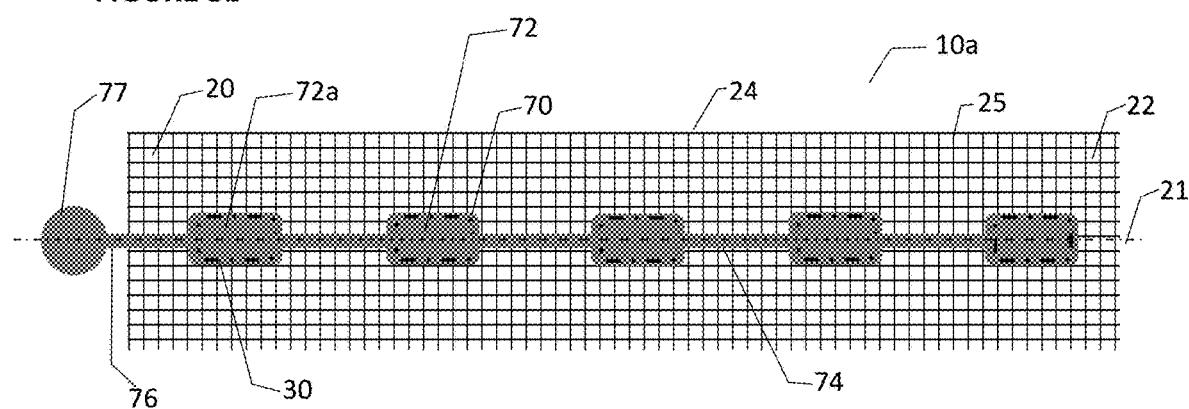
FIG. 3b shows an embodiment of the skin closure device in a schematic top view.

Referring now to FIG. 3b which shows mesh 20 of FIG. 1a, with mask 70 shown positioned on top of mesh 20 on upper side 22, with mask 70 aligned along longitudinal axis 21 and with masking segments 72 in registration over windows 30 and completely covering windows 30. Windows 30 are shown schematically in FIG. 3B in dashed line as visible through masking segments 72, which are shown slightly overlapping windows 30.

Lift-up tab 76 is shown linearly extending from masking segment 72a at one end of mask 70, extending beyond and outside of mesh 20. Lift-up tab 76 is shown having an optional grasping portion 77, which a larger and wider area of lift-up tab positioned outside of mesh 20.

There is an optional pressure sensitive adhesive (not shown) applied on mask 70 surface facing mesh 20, facilitating mask 70 being peelably or removably immobilized on upper side 22 of mesh 20. Pressure sensitive adhesive also helps to prevent adhesive 50 penetrating and contacting areas of wound in the areas of windows 30. In one embodiment, there is no PSA on connectors 74 surfaces facing mesh 20, to facilitate adhesive 50 flowing under connectors 74, but only PSA present is PSA on masking segments 72 surfaces facing mesh 20 and windows 30, to further prevent adhesive 50 penetrating under masking segments 72 and contacting areas of wound in the areas of windows 30.

Embodiments with mask 70 can be applied to any of the shown device embodiments 10a, 10b, 10c, i.e. mask 70 can be utilized with and without flap 60, and absorbent insert 68.

In one embodiment, there is a pH modifying coating on top of connectors 74 and masking segments 72 that slows down or inhibits polymerization. The coating can be any chemistry that prevents or slows down polymerization, such as acidic based materials, acids, salts, and buffers, which are characterized in bringing neutral pH=7 to pH values below 7.0 when dissolved in water.

Examples include salts of ammonium (NH4+); methyl ammonium (CH3NH3+); ethyl ammonium (CH3CH2NH3+); anilinium (C6H6NH2+) as well as salts with hydrolysable protons in the anion, including e.g. bisulfate (HSO4-); dihydrogen citrate (H2C6H5O7-); bioxalate (HO2C2O—). Examples of salts can include NaHSO4, NaH2PO4, NH4Cl, anilinium chloride, etc.

Figure 3C:
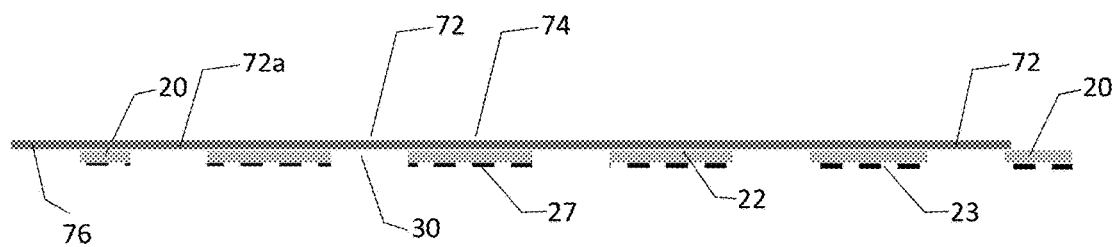
FIG. 3c shows an embodiment of the skin closure device in a schematic side cross-sectional view.

Referring now to FIG. 3c which is a side cross-sectional view of mesh 20 similar to FIG. 1c, FIG. 3c shows side cross-sectional view of device of FIG. 3b with mesh 20 having mask 70 disposed on upper side 22.

Preferably, the dimensions of connectors 74 are selected so that when mask 70 positioned on top of mesh 20 is covered by a liquid polymerizable adhesive 50, adhesive is penetrating under connectors 74 and substantially or fully covers areas of mesh 20 under connectors 74, preventing formation of areas devoid of adhesive 50 under connectors 74. As used herein, "substantially cover(s)" is intended to describe sufficient covering of the device with adhesive to maintain the wound or incision in a closed or approximated state sufficient for the intended purpose of closing the wound or incision.

Advantageously, dimensions of windows 30 and masking segments 72 are selected so that adhesive 50 is not fully penetrating under masking segments 72 and substantially not covering areas of windows 30, while dimensions of connectors 74 are selected so that adhesive 50 is penetrating under connectors 74 and substantially or fully covers areas of mesh 20 under connectors 74.

Experimental testing of width of connectors 74 as strips of masking films was performed on simulated skin substrates. Polymerizable adhesives with varying viscosity were used, specifically viscosity~8 cP and 200 cP. Adhesive was applied over strips of shielding film of varying width immobilized on a mesh using PSA. Within 0.5-5 minutes of application, shielding film strips were lifted or peeled and the penetration of liquid adhesive under strips of shielding film was evaluated. The results show that liquid adhesives of 8 cP viscosity have fully penetrated under strips 3 mm wide, partially penetrated under strips 7 mm wide, and not substantially penetrated under strips 11 mm wide. Liquid adhesives of 200 cP viscosity have partially penetrated under strips 3 mm wide, and not substantially penetrated under strips 7 and 11 mm wide.

According to some embodiments, connectors 74 width is selected to ensure full penetration of liquid adhesive used (with a given viscosity) under connectors 74. According to some embodiments, masking segments 72 width is selected to ensure no penetration or only minor limited penetration of liquid adhesive used (with a given viscosity) under masking segments 72.

According to one embodiment, width of connectors 74 is 3 mm or less, while width of masking segments 72 is 7 mm or more. According to another embodiment width of masking segments 72 is 11 mm or more. According to one embodiment, the mask as described is sized for use with adhesives having 8 cP viscosity or 200 cP viscosity.

According to one embodiment, the mask as described is sized for use with adhesives having viscosity from 8 cP to 200 cP.

Figure 4A:
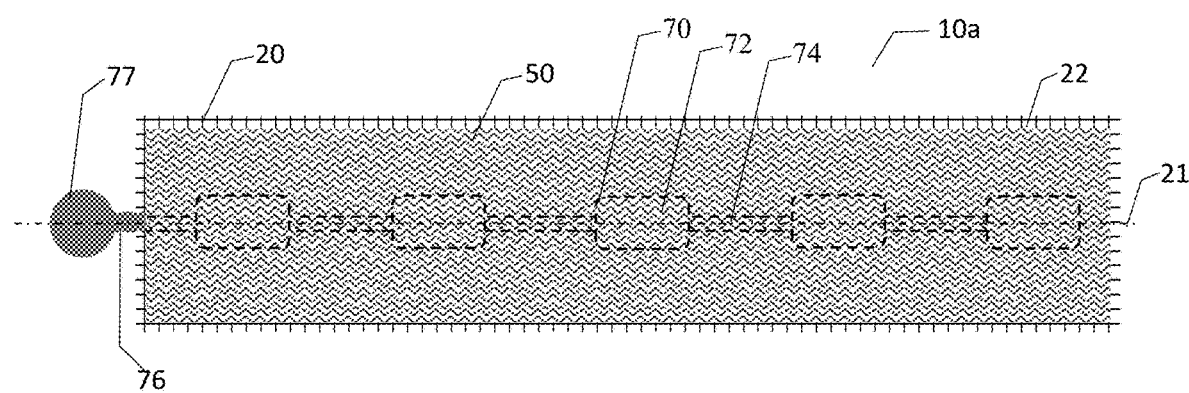
FIGS. 4a-b show embodiments of the skin closure device in a schematic top view during use of the device.

In use, and further referring to FIG. 4*a*, similarly to descriptions related to embodiments of FIG. 1*f,* mesh 20, after removal of optional liner material covering lower side 23, is positioned on a wound with lower side 23 facing the wound (not shown). Mesh 20 is secured to wound surface (such as skin) by traces of PSA (not shown). Optionally, mesh 20 is used to approximate and hold in apposition or close approximation the edges of surgical incision or wound, using traces of PSA for securement of mesh 20 and for securing in close approximation or apposition the edges of surgical incision or wound.

Generally longitudinal axis 21 is aligned and superimposed over the wound. The positioning of device 10*a* over the surgical incision or wound is performed so that axis 21 is as much as possible aligned with the surgical incision or wound and overlaps with the surgical incision or wound i.e., axis 21 is in registration the surgical incision or wound.

Figure 4B:
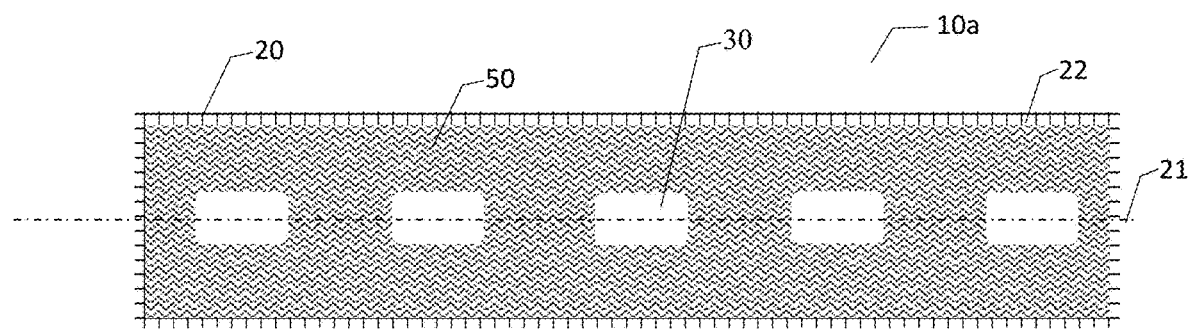

Liquid polymerizable or cross-linkable adhesive 50 is then uniformly and rapidly applied over the whole of mesh 20 upper surface 22, including over mask 70, which is shown schematically in dashed lines as fully covered by adhesive 50. The liquid adhesive is also applied over areas corresponding to windows 30 (not visible in FIG. 4*a* under masking segments 72) which are fully covered by masking segments 72. Adhesive 50 is then penetrating through mesh 20 and establishing contact with skin 100 (not shown) in all areas not covered by masking segments 72, including under connectors 74. Liquid adhesive 50 starts then polymerizing and/or cross-linking, but before full polymerization and/or cross-linking and solidification of adhesive 50, mask 70 is lifted or peeled from mesh 20, preferably by manually pulling on tab 76 and/or optional grasping portion 77 and pulling in the direction opposite mesh 20 so as to remove mask 70 from mesh 20. It is preferred to remove mask 70 before full solidification and polymerization of adhesive 50. Mask 70 covered by adhesive 50 is then discarded, leaving mesh 20 with established secure bond with skin or wound and with windows 30 free of adhesive 50 and not covered by adhesive 50, as shown in FIG. 4*b*. Skin closure by device 10*a* is thus completed with surgical incision under mesh 20 securely covered and closed, with adhesive 50 rapidly applied despite complex windows pattern, and with windows 30 providing areas of wound which are non-covered by adhesive 50, allowing for drainage, inspection, and access.

Advantageously, use of mask 70 enables rapid application of adhesive 50 over the whole surface of device 10, with no need in carefully applying adhesive around windows 30 and avoiding adhesive getting into windows 30. This facilitates fast and easy to deploy application of devices 10, including embodiments 10*a*, 10*b*, 10*c*. Advantageously, after such rapid application of adhesive 50 over the whole surface, rapid manual removal of mask 70 leaves tissue and/or wound and/or skin exposed through windows 30.

Sizes/Dimensions/Materials

Flexible mesh 20, liner 40, flap or cover 60, mask 70, are made of any suitable biocompatible polymeric material, natural, synthetic polymer, or combinations thereof. Exemplary materials include polyethylene, polypropylene, polyester, etc. Absorbent and removable insert 68 can be made of any fluid-absorbing, biomedically compatible material such as natural or synthetic polymer, or combinations thereof. It can comprise polyethylene, polypropylene, polyester, cellulose, oxidized cellulose, carboxymethylcellulose, cotton, modified cotton, or generally any absorbent and/or spongy and/or fibrous biocompatible material.

Mesh 20 can be of any elongated shape to cover a wound, such as elliptical, rectangular, and similar. Mesh 20 can have ratio of length to width of about 1:2 to about 1:20, such as 1:5. The length of mesh 20 is from about 10 cm to about 50 cm, such as 25 cm. The width of mesh 20 is from 2 cm to 10 cm, such 3 cm, 5 cm.

Elongated traces 27 of pressure sensitive adhesive (PSA) have width from about 0.5 mm to about 7 mm, more preferably 1 mm to 5 mm, such as 1, 1.5, 2, 3, 4 mm. The length of elongated traces 27 is from about 50% of the width of mesh 20 to about 300% of the width of mesh 20, such as 10, 15, 20, 30, 40, 50, 60 mm. The length of elongated traces 27 is from about 50% to about 100% of the length of mesh 20, such as 50, 100, 200, 300 mm.

PSA

PSA materials are exemplified by water soluble pressure sensitive adhesives, including hydrocolloids; homo-polymer emulsion (PVA); water-based acrylic adhesives; polyurethane dispersions (PUDs); polyethylene glycol; dextrin/starch-based adhesives; N-vinyl pyrrolidone copolymers; polyvinyl alcohol; cellulose ethers; methylcellulose; carboxymethylcellulose; polyvinylpyrrolidone; polyvinyl acetates, or by water insoluble pressure sensitive adhesives, including acrylic adhesives; cyanoacrylate adhesives; epoxy; silicone based adhesives; and urethane.

Initiator

In a preferred embodiment, initiators and/or accelerators or rate modifiers of adhesive polymerization or cross-linking can be releasably disposed on mesh 20 or releasably incorporated into mesh 20. For example, one or more chemical substances may be dispersed in or on mesh 20 such as being chemically bound, physically bound, coated, absorbed, or adsorbed to it.

For example, a polymerization initiator or accelerator or rate modifier may be loaded in or on mesh 20 so that the initiator or rate modifier provides the desired initiation or rate modification effect to a subsequently applied polymerizable adhesive composition. The polymerization initiator or rate modifier may be immobilized in or on mesh 20, so that the initiator or rate modifier does not become detached from mesh 20 and its residues are dispersed in the resultant polymeric material. Alternatively, for example, the polymerization initiator or rate modifier may be initially attached to mesh 20, but only in such a manner that it becomes mobilized or solubilized by a subsequently applied polymerizable adhesive composition and dispersed in the resultant polymeric material.

If desired, a combination of chemical substances may also be provided in or on mesh 20, to provide multiple effects. For example, a first chemical species (such as a polymerization initiator or rate modifier) may be immobilized in or on mesh 20, while a second, different chemical species (such as a bioactive material) may be detachably attached to mesh 20. Other combinations of chemical species and resultant effects are also envisioned.

When present in or on mesh 20, the chemical substances (i.e., polymerization initiator, rate modifier, and/or bioactive materials, or other additives), may be incorporated in or on mesh 20 in any suitable manner. For example, the chemical substance may be added to mesh 20 by contacting mesh 20 with a solution, mixture, or the like including the chemical substances. The chemical substance may be added to mesh 20, for example, by dipping, spraying, roll coating, gravure coating, brushing, vapor deposition, or the like. Alternatively, the chemical substance may be incorporated into or onto mesh 20 during manufacture of mesh 20, such as during molding.

The polymerization initiator or rate modifier loaded in or on mesh 20 may provide a number of advantages for example, so as to provide faster polymerization time. The concentration of polymerization initiator or rate modifier may be increased to provide even faster polymerization time. Because the polymerization initiator or rate modifier is loaded directly in or on mesh 20, it is not necessary to mix the polymerizable adhesive composition with a polymerization initiator or rate modifier prior to application. This may allow a longer working time, where the polymerizable monomer composition may be more precisely and carefully applied over a longer period of time. Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used. Benzalkonium or benzyltrialkyl ammonium halides such as benzyltrialkyl ammonium chloride may be used. When used, the benzalkonium halide may be benzalkonium halide in its unpurified state, which comprises a mixture of varying chain length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfite, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics.

Adhesive

In one embodiment, liquid or semi-liquid adhesive 50 is polymerized or is crosslinked polymerized or is cross-linked after coming in contact with initiators and/or accelerators of adhesive polymerization and/or cross-linking, including naturally found initiators on the tissue, such as moisture, traces of proteins, etc. Such initiators and/or accelerators can be coated or disposed non-releasably, i.e. immobilized in or on the mesh 20 while retaining activity to initiate or accelerate polymerization and/or cross-linking. In one embodiment, initiators and/or accelerators are disposed releasably, i.e., they can be at least partially released into and mix with flowing adhesive 50.

In a preferred embodiment, adhesive 50 is polymerized or is cross-linked after coming in contact with initiators and/or accelerators releasably disposed in or on mesh 20. Rapid polymerization and/or crosslinking of adhesive 50 results in bonding of device 10 to tissue.

Adhesive 50 can be any type of biocompatible and rapidly cross-linkable and/or polymerizable compound or mixture of compounds. Rapidly cross-linkable and/or polymerizable means that after initiators or accelerators are added, or after the adhesive is formed from two or more components, it is capable of curing, i.e. cross-linking and/or polymerizing within 0.2 min to about 20 min, more preferably within 0.5 min to 10 min, such as 1, 2, 3, 5 min.

In one embodiment, adhesive 50 is formed prior to application onto mesh 20, for instance by mixing two components contained in separate barrels or a two-barrel syringe, by passing these two components through a mixing tip. In this embodiment, there is no crosslinking initiator or accelerator disposed inside of mesh 20. In one embodiment, adhesive 50 is formed by mixing fibrinogen and thrombin together.

In one embodiment, adhesive 50 comprises fibrinogen, and crosslinking initiator or accelerator disposed inside of mesh 20 comprises thrombin.

In a preferred embodiment, the polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable .alpha.-cyanoacrylate monomers which may be used, alone or in combination, include alkyl .alpha.-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other .alpha.-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl .alpha.-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Many other adhesive formulations can be used and are known to a skilled artisan. For example, mixtures containing PEG succinimidyl glutarate can be used as a flowable adhesive.

Use of the Inventive Skin Closure Systems

In one embodiment, application of the inventive devices to a wound is performed in the following sequence of steps. Please refer to the figures for identification of reference numerals used below.

Follow standard surgical practice for wound preparation for thorough wound cleansing before application of inventive devices 10a, 10b, 10c, i.e., cleanse, irrigate, debride, obtain hemostasis and close deep layers such that there is no tension on the skin edges. The skin edges must be closely approximated prior to application of the instant devices, so that that significant manual approximation is not required during mesh 20 application.

Pat the wound dry with dry, sterile gauze to ensure direct tissue contact for adherence of mesh 20 and the adhesive 50 to the skin 100.

Aseptically transfer device 10a, 10b, or 10c and liquid adhesive in a suitable container to the sterile field.

Referring in particular to FIGS. 1d, 1e, and 1f, remove the central segment 40b of the release liner 40 from mesh 20. While removing first the central segment 40b is preferred, alternative sequences can entail removing both central segment 40b and one peripheral segment 40a simultaneously. Yet another alternative sequence can entail removing first only one peripheral segment 40a.

Hold mesh 20 by the corners of the liner 40, ensuring pressure-sensitive adhesive (PSA) 27 will be on the mesh 20 lower side 23 that will be adhered to the patient's skin 100.

Position mesh 20 so one half is on either side of the incision or wound 110, ensuring approximately 1 cm of mesh 20 extends from the beginning of incision 110. Press gently to ensure intimate contact of mesh 20 to the selected side of incision 110. Gently pull mesh 20 perpendicularly over incision 110 while adjusting with fingers or forceps to achieve skin edge approximation and affix the remainder of mesh 20 to the other side of incision 110. If there are areas where mesh 20 is loose, gently pass a gloved finger or instrument over the affected area to ensure complete adherence of mesh 20 to the skin 100.

Remove remaining liner 40 segments, such as segments 40a, 40c.

Trim mesh 20 if necessary, ensuring at least 1 cm of mesh 20 extends beyond the end of incision 110. Ensure that mesh 20 is in intimate contact with skin 100 prior to application of liquid adhesive 50.

The liquid adhesive 50 should be applied over mesh 20 immediately after mesh 20 has been placed. Pat the deployed mesh 20 dry gently with dry sterile gauze in the event of bodily fluid seepage without disturbing skin edge approximation prior to spreading the adhesive over mesh 20.

Referring generally to FIGS. 3a, 3b, 3c, 4a and 4b, spread liquid adhesive 50 smoothly and evenly over the entire length of meshes 20 and optionally surrounding skin area using a suitable flexible applicator tip. Apply liquid adhesive 50 using short strokes and moving from one end of mesh 20 to the other, making sure that mesh 20 is saturated as liquid adhesive 50 is applied along the entire length L. Liquid adhesive 50 can also be applied slightly over the edge of mesh 20, covering a small margin of surrounding skin.

For embodiments without mask 70, apply liquid adhesive 50 on top of mesh 20 avoiding windows 30, i.e. without applying adhesive through windows 30.

For embodiments with mask 70, apply liquid adhesive 50 on top of mesh 20 and also on top of mask 70, i.e. covering areas of windows 30 covered by mask 70.

After applying liquid adhesive 50, for embodiments with mask 70, lift and discard mask 70 immediately, preferably prior to complete polymerization of adhesive 50.

Once applied to mesh 20, after about 1 min, check that polymerization is complete by gently dabbing along the length of mesh 20 with a gloved finger, checking for tackiness. When no liquid or tackiness is apparent, the polymerization process is complete. Once the liquid adhesive is polymerized, flap 60 of embodiments 10b, 10c can be closed over mesh 20 by folding over upper side 22.

It should be understood that the foregoing disclosure and description of the embodiments of the present invention are illustrative and explanatory thereof and various changes in the size, shape and materials as well as in the description of the preferred embodiment may be made without departing from the spirit of the invention.

We claim:

1. A device for application onto incisions or wounds with a liquid rapidly polymerizable adhesive for forming skin closure systems, comprising
 a flat porous mesh elongated along a longitudinal axis and having an upper side and an opposing lower or wound facing side and a central portion in immediate vicinity of the axis;
 further having a plurality of pores and windows in said mesh, said windows substantially larger than said pores and arranged along said longitudinal axis in said central portion;
 a crosslinking or polymerization accelerator or initiator disposed in or on said mesh; and a pressure sensitive adhesive disposed on at least a portion of the lower surface of said mesh.

2. The device of claim 1, further comprising
a flat cover attached to said mesh at an edge of said mesh;
said cover configured to be foldable over the upper side of said mesh in a book-like fashion and sized to as least partially cover said mesh and to fully cover said windows.

3. The device of claim 2, wherein said cover is further comprising
a pressure sensitive adhesive disposed on a side of said cover facing the upper side of said mesh.

4. The device of claim 2, wherein said cover is releasably adhering to the upper side of said mesh.

5. The device of claim 2, wherein said cover is partially or fully transparent.

6. The device of claim 2, further comprising
a plurality of absorbent pads attached to said mesh at the edge of said mesh and sized to cover said windows,
said absorbent pads disposed in a book-like arrangement between said flap and said mesh and foldable over the upper side of said mesh.

7. The device of claim 6, wherein
said absorbent pads further comprise a tear-off line and are configured for easy tear-off from the edge of said mesh.

8. The device of claim 1, further comprising
a mask comprising an elongated, flexible, flat strip comprising a plurality of masking segments arranged along said strip and interconnected by narrow connectors;
said mask having a mesh-facing surface and an opposing top surface;
said masking segments configured and sized to completely cover said windows when the mask is disposed on the mesh;
with spacing between masking segments matching corresponding spacing between windows with the masking segments in registration over the windows;
said mask further comprising a lift-up tab linearly extending at one end of the mask;
said mask removably attached with mesh-facing surface onto the upper side of the mesh with the masking segments covering the windows.

9. The device of claim 8, wherein
said mask is further comprising a pressure sensitive adhesive disposed on the mesh-facing surface.

10. The device of claim 9, wherein
said pressure sensitive adhesive is present on the masking segments and not present on the connectors.

11. The device of claim 8, further comprising
a pH modifying coating on the top surface of said mask, configured to slow down polymerization.

12. The device of claim 8, wherein
dimensions of the masking segments and of the connectors are configured so that the adhesive is not fully penetrating under the masking segments and fully penetrating under the connectors.

13. The device of claim 1, wherein the adhesive has viscosity from 8 cP to 200 cP.

14. The device of claim 1, wherein the accelerator or the initiator comprises quaternary ammonium salt.

15. The device of claim 1, wherein the adhesive comprises cyanoacrylate monomers, fibrinogen, or PEG succinimidyl glutarate.

* * * * *